(12) United States Patent
Johns

(10) Patent No.: US 7,071,831 B2
(45) Date of Patent: Jul. 4, 2006

(54) ALERTNESS MONITOR

(75) Inventor: Murray Johns, Richmond (AU)

(73) Assignee: Sleep Diagnostics Pty., Ltd., Victoria (AU)

( * ) Notice: Subject to any disclaimer, the term of this patent is extended or adjusted under 35 U.S.C. 154(b) by 142 days.

(21) Appl. No.: 10/488,960

(22) PCT Filed: Nov. 7, 2002

(86) PCT No.: PCT/AU02/01508

§ 371 (c)(1),
(2), (4) Date: Mar. 9, 2004

(87) PCT Pub. No.: WO03/039358

PCT Pub. Date: May 15, 2003

(65) Prior Publication Data

US 2004/0233061 A1    Nov. 25, 2004

(30) Foreign Application Priority Data

Nov. 8, 2001 (AU) .................... PR8723

(51) Int. Cl.
*G08B 23/00* (2006.01)

(52) U.S. Cl. ..................... 340/576; 340/575

(58) Field of Classification Search ............... 340/575, 340/576, 5.81; 128/898; 600/300, 500, 600/544, 545, 546, 558; 351/210, 221, 209; 382/117
See application file for complete search history.

(56) References Cited

U.S. PATENT DOCUMENTS

| 4,838,681 | A | * | 6/1989 | Pavlidis | 351/210 |
| 5,583,795 | A | * | 12/1996 | Smyth | 702/150 |
| 5,867,587 | A | * | 2/1999 | Aboutalib et al. | 382/117 |
| 6,575,902 | B1 | * | 6/2003 | Burton | 600/300 |
| 6,743,022 | B1 | * | 6/2004 | Sarel | 434/236 |
| 6,947,790 | B1 | * | 9/2005 | Gevins et al. | 600/544 |

* cited by examiner

*Primary Examiner*—Van T. Trieu
(74) *Attorney, Agent, or Firm*—Connolly Bove Lodge & Hutz LLP

(57) ABSTRACT

An alertness monitoring system includes: means to measure velocity and amplitude of eyelid and eye movement; and storage means to continuously record the measurements. A data processor calculates the blink amplitude to velocity ratio and/or the saccade amplitude to velocity ratio and compares the measurements against a predetermined scale. The scale is derived from averaged measurements of the eye and eyelid movement parameters for a sample population measured against predetermined incremental blood alcohol levels. The output of the system can include a display for showing the alertness measurement based on the scale, or an alarm means triggered by the scale reading reaching a predetermined limit based an the blood alcohol level scale.

18 Claims, 10 Drawing Sheets

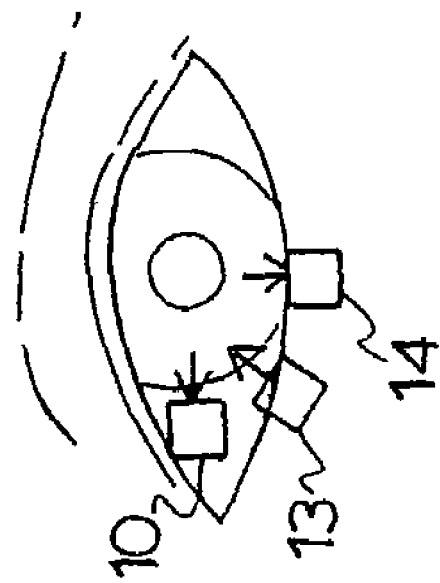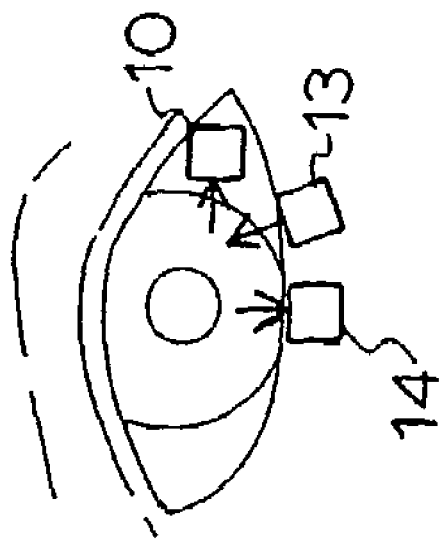
FIG. 1.

ALERTNESS MONITOR

This invention relates to a method and device for testing alertness and the onset of drowsiness by monitoring eye and eyelid movement.

BACKGROUND TO THE INVENTION

The detection of drowsiness is of importance because drowsiness impairs the ability of operators of a wide range of equipment including motor vehicles, aircraft and boats as well as industrial equipment. The problem of drowsy driving cannot be solved by educating drivers to take remedial action when feeling drowsy. The difficulty is that many people are unaware of their drowsiness before and during the drowsiness even though they may be alert and aware after they rouse. This means one cannot predict when their level of drowsiness will next decrease to the point of danger because the drowsy state involves a loss of awareness of the present; an involuntary lapse of attention.

U.S. Pat. No. 5,745,038 discloses an eye monitor that examines reflected light from the eye to detect blinking behavior as an indicator of drowsiness.

U.S. Pat. No. 5,867,587 discloses a system which utilises digital images of the face and eyes of an operator, derives a parameter attributable to an eye blink and compares this to a threshold value of that parameter. A warning signal is given if the parameter falls below the threshold.

Patent specification WO 98/49028 also uses a video image as an eye gaze monitor to view a range of eye movements and analyse and compute a degree of alertness.

U.S. Pat. No. 6,091,334 discloses a system for analysing drowsiness which monitors head movement and gaze stability.

U.S. Pat. No. 6,102,870 uses eye tracker data such as fixations and saccades to infer mental states of the operator such as scanning, reading, searching, thinking and an intention to select. It is a system to enhance computer software responsiveness.

U.S. Pat. No. 6,097,295 discloses a system of image analysis based on eye pupil size.

U.S. Pat. No. 6,147,612 discloses a system of preventing sleep which detects eyelid movement and actuates an alarm when the eyelid movement is indicative of drowsiness.

U.S. Pat. No. 6,346,887 uses a video based eye tracking system which tracks eye activity and pupil diameter and position to produce a signal representing eye activity that can be used to estimate alertness.

All of the above approaches fail to provide a real time alertness monitor that can provide a calibrated measure of the operator's alertness. It is an object of this invention to provide an alertness monitor that provides an objective and calibrated measure of the operator's fitness to operate a vehicle or machinery.

BRIEF DESCRIPTION OF THE INVENTION

To this end the present invention provides an alertness monitoring system which includes
a) means to measure eyelid and eye movement for presence of one or more of relatively slow eye and eyelid movements in relation to their amplitude, wavering eyelids, partial eye closure, drooping eyelids; slow or drifting eye movements, slow and prolonged eyelid closure, absence of saccadic movement and loss of eye co-ordination
b) storage means to continuously record the measurements
c) a data processor to compare the measurements against a pre determined scale, said scale being averaged measurements of the eye and eyelid movement parameters for a sample population measured against predetermined incremental blood alcohol levels
d) a display for showing the alertness measurement based on the scale or
e) an alarm means triggered by the scale reading reaching a predetermined legal limit based on the blood alcohol equivalent scale.

This invention is predicated on a realisation that changes in eye and eyelid movements are an early and reliable indication of drowsiness and alertness loss. More particularly this invention is predicated on the realization that the peak velocity of normal saccadic eye movements and of eyelid closure during blinks varies with the amplitude of those movements. It has been discovered that with drowsiness the velocities are lower for the same amplitude. The ratio of amplitude to peak velocity for blinks and saccades increases with the level of drowsiness. Because the dimension of this ratio is time neither the amplitude nor the velocity needs to be measured in absolute terms so long as the measurements involve the same arbitrary scale. In the device of this invention it is volts.

This invention is also based on the realisation that blood alcohol levels have effects on eye movements that parallel the effects of drowsiness. That is drowsiness, loss of alertness and blood alcohol induce behavioural states that show the same patterns of eye and eyelid movements. In laboratory settings impairment in performance of many psychophysiological tests because of progressively longer sleep deprivation that causes increasing levels of drowsiness has been correlated with the equivalent effects that increasing blood alcohol concentrations have on the performance of those tests.

It is a benefit of this invention that the monitor can continuously record the operators alertness as being equivalent to that associated with a blood alcohol content. Many countries have legislated that it is illegal to drive a vehicle or have control of machinery etc with a blood alcohol level above specified values. Therefor this invention enables drowsy operators to be judged as if they were impaired by alcohol and provide a measure of legal fitness to operate a vehicle or machinery.

In another aspect of this invention there is provided An alertness measuring system for a subject which includes
a) an infrared pulse emitter adapted to be located adjacent at least one eye of a subject
b) at least one reflected light detector located adjacent said emitter
c) means to transmit the detector signals
d) data processing means to receive the detector signals and to subtract the total level of light immediately before each pulse is transmitted from the combined level of the measured reflectance during the pulse to provide a reflectance measure
e) said data processing means analyzing said reflectance measure to assess eyelid and eye movement for presence of one or more of relatively slow eye and eyelid movements in relation to their amplitude, wavering eyelids, partial eye closure, drooping eyelids; slow or drifting eye movements, slow and prolonged eyelid closure, absence of saccadic movement and loss of eye co-ordination.

It is preferred to use reflectance off both eyes as a means of measuring eye and eyelid movement. Infrared light sources and detectors may be mounted on the face, near the eyes, to measure the changes in light reflected back from each eye. One detector can be adjacent the emitter and one may be across the eye to best detect eyelid closure. These emitters and detectors can communicate with a computer based analysis and recording system by wire or wireless [radio frequency] connection.

The reflectance data may be analysed into several frequency domain or time domain ranges to obtain relative position and velocity data for each eye that can be analysed to show presence of relatively slow eye and eyelid movement, eyelid closure, impairment of binocular co-ordination of the eyes and prolonged ocular quiescence.

The data recorded may be continually compared to pre-recorded data, which averages the saccadic movement data of a population sample measured at incremental levels of blood alcohol content. This data, which establishes the correlation between eye movement blood alcohol content and reduction in alertness, is stored in a form accessible for comparison against the data being recorded. The stored data may be in the form of a look up table or an image display. The recorded data used for comparison is a set of readings of several parameters of eye movement over a predetermined duration generally 5 to 60 seconds which is continually updated. When this matches a set of data for a particular blood alcohol content that blood alcohol value is recorded as the alertness level of the operator.

Vision is blocked by eyelid closure but detecting such closure is not enough to detect all drowsiness episodes. Even when eyelids are open very drowsy subjects still cannot see due to central or neural blocking of vision and impaired oculomotor control. Neural blocking occurs during blinking and saccade movement although subjects are unaware that vision is temporarily switched off at these times. Some drowsy subjects striving to stay awake do keep their eyelids open for a number of seconds after they begin to lose oculomotor control particularly binocular coordination of eye movements. The first subjective awareness of this would be double vision or diplopia. Subjects are not usually aware of subsequent slow and poorly coordinated eye movements, presumably due to neural blocking of vision.

By comparison the subjects head is unlikely to nod forward until drowsiness has progressed to sleep. Consequently a nodding head may be a late warning of dangerous drowsiness.

The device of this invention monitors the relative positions and movements of the eyes and eyelids. With the onset of drowsiness the mean duration of spontaneous blinks blinks increase from about 300 milliseconds to more than 450 milliseconds. Eventually eyelid movements become so slow that they are no longer blinks but slow eyelid closures which occur intermittently and last from a half to several seconds. During the waxing and waning of alertness and drowsiness that is typical of this state other eyelid movements occur such as partial blinks and wavering movements of the lids that need to be distinguished from slow eye movements. The I R reflectance used in this invention allows the distinction to be made.

In another aspect of this invention there is provided a method of measuring alertness in which the eye movements of a subject are analysed using reflected infra red light pulses to obtain measures of the blink amplitude to velocity ratio and/or the saccade amplitude to velocity ratio averaging these over predetermined periods of time and measuring the deviation of the average from a predetermined average for alert subjects.

BRIEF DESCRIPTION OF THE FIGURES

FIG. 1 is a schematic diagram showing the location of the emitters and detectors

DETAILED DESCRIPTION OF THE INVENTION

Referring to FIG. 1 each eye is provided with an infra red pulse emitter 10 and two infra red reflectance detectors 13 and 14. Detector 13 detects reflected light horizontally across the eye which corresponds to the movement of the eyeball and detects saccadic movement from which the amplitude and velocity of each saccade can be derived to provide a saccade amplitude to velocity ratio. Detector 14 detects reflected light vertically across the eye which corresponds to the movement of the eyelid and detects eyelid movement from which the amplitude and velocity of each blink can be derived to provide a blink amplitude to velocity ratio. The subject wears a light supporting frame to hold the light emitters and detectors. The device is akin to the lower half of a spectacle frame and does not restrict the wearer's field of vision. A second part which can be in a pocket or attached to a belt contains the pulse generating and timing circuitry and the transmitter.

Figure 2:
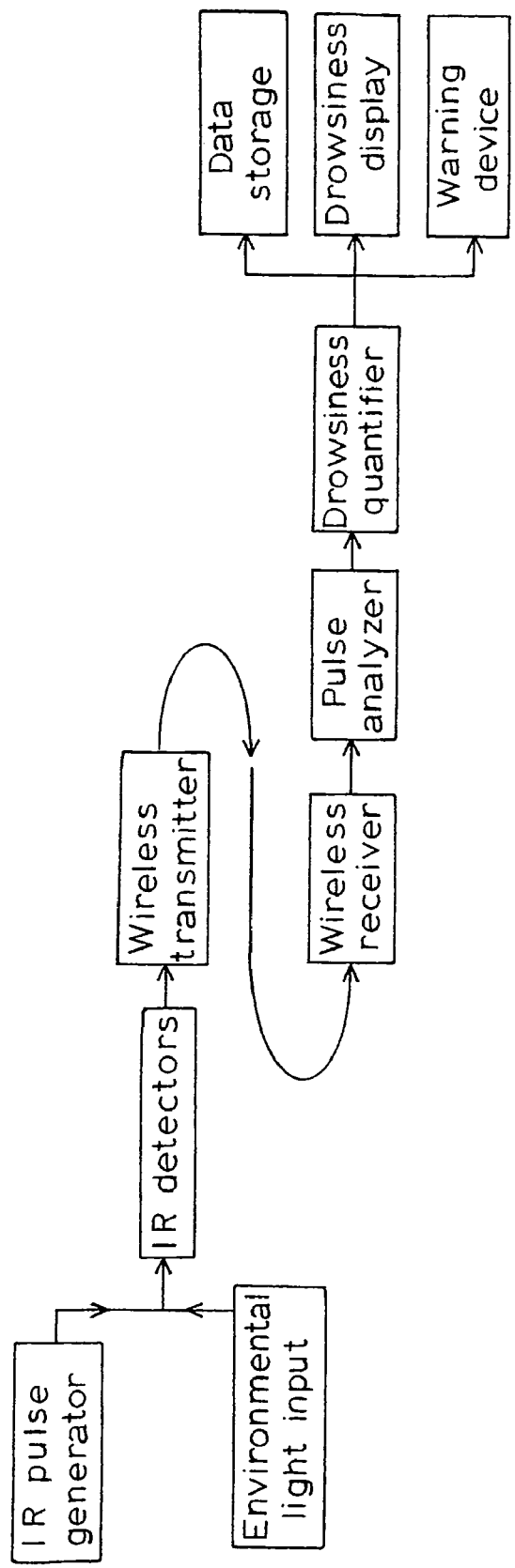
FIG. 2 is a schematic layout of the system function according to this invention.

As shown in FIG. 2 the system of this invention uses IR pulse generators an IR detector and a wireless transmitter to transmit the detected signals to a receiver. The reflected infrared pulse height varies as the eye and eyelid move. The LED's preferably send out 50 microsecond duration pulses every 500 microseconds (that is 2000 times a second).

The receiver sends the signals to a pulse analyzer that measures the height of each reflected IR pulse (in volts) after subtracting the effects of environmental light. It then analyses the data in several ways including comparisons between the two eyes.

The out put of the drowsiness quantifier can be stored, displayed or used to actuate an alarm when a threshold condition is passed. The control portion of the device which contains the display and alarm incorporates a micro processor programmed to analyse the received signals. The memory store contains data about the subject's drowsiness over a preceding time period and can be used much as a black box is used for aircraft accidents should an accident occur. The device does not require calibration before each use.

In night driving the levels of environmental light both visible and IR can change rapidly as with the headlights of oncoming traffic approaching and rapidly passing or with day driving when sunlight is interrupted by trees. All such sources of IR light can be detected on the subject's face. For this reason the device of this invention measures the total level of light immediately before each pulse is transmitted and subtracts this from combined level of the pulse and environment. This means the device can be used in all light conditions from bright sunlight to night conditions. The amount of IR light reflected is related to the position of the eyes due to the conical shape of the cornea and to the position of the eyelids ands also to differences in reflectance of the tissues exposed when eyelids are open and when closed. The I R pulses directed to each eye are separated in time by about 100 microseconds to avoid interference.

The levels and patterns of change in the light reflected from each eye enable the relative positions of each eye and eyelid to be monitored continuously. The device can detect and distinguish vertical and horizontal movements including saccadic and slow eye movements such as those in smooth pursuit of a target or because of vestibular-ocular movements that enable ocular fixation in spite of head movements.

Figure 3:
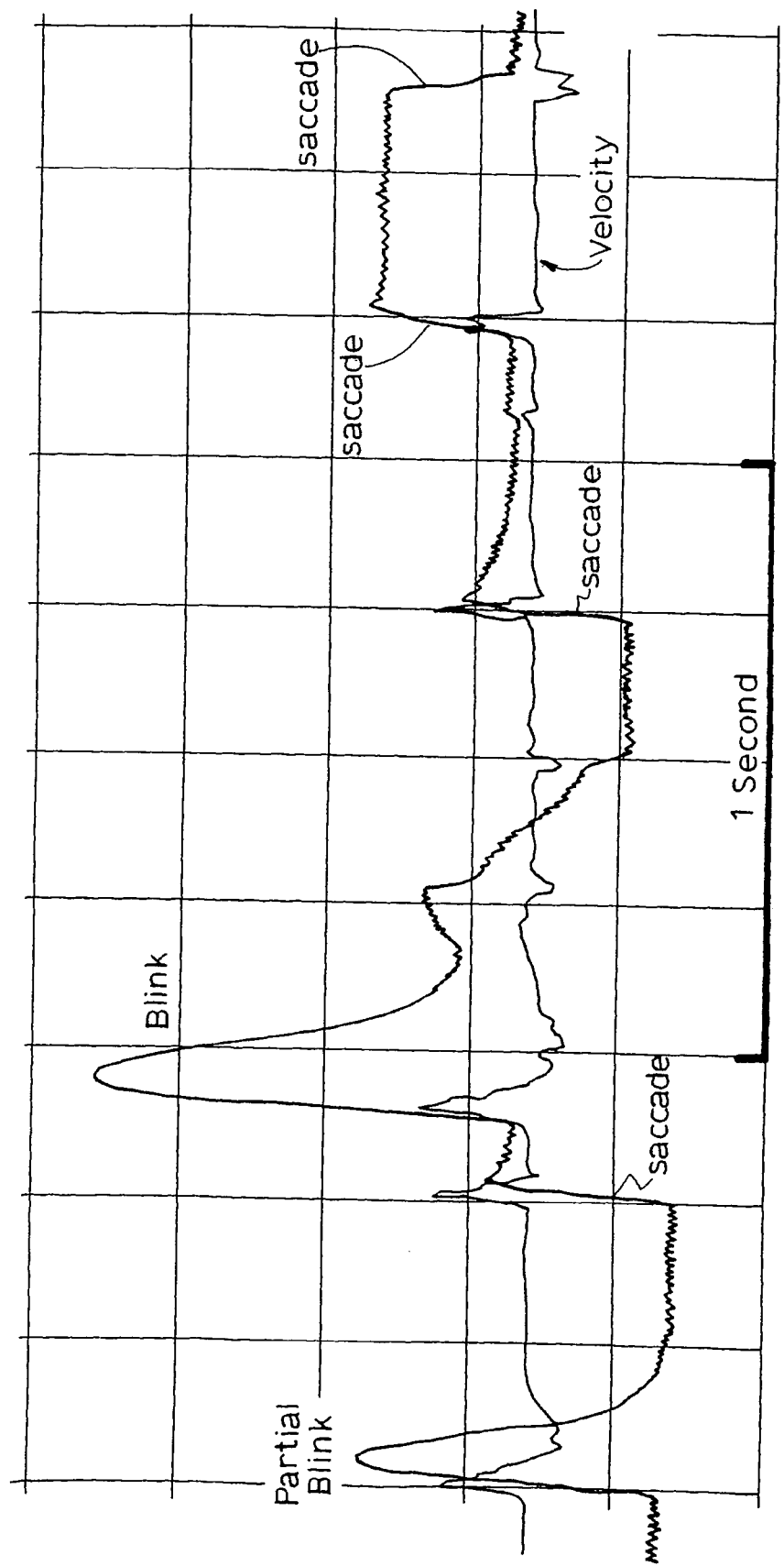
FIG. 3 is an example of a graphical output of this invention relating to eye lid movement.

FIG. 3 illustrates the reflectance signal from a series of normal saccades and blinks. This data is analysed to identify signal patterns relating to loss of bi-ocular co-ordination, slow saccades, partial and slow eye closure.

Figure 4:
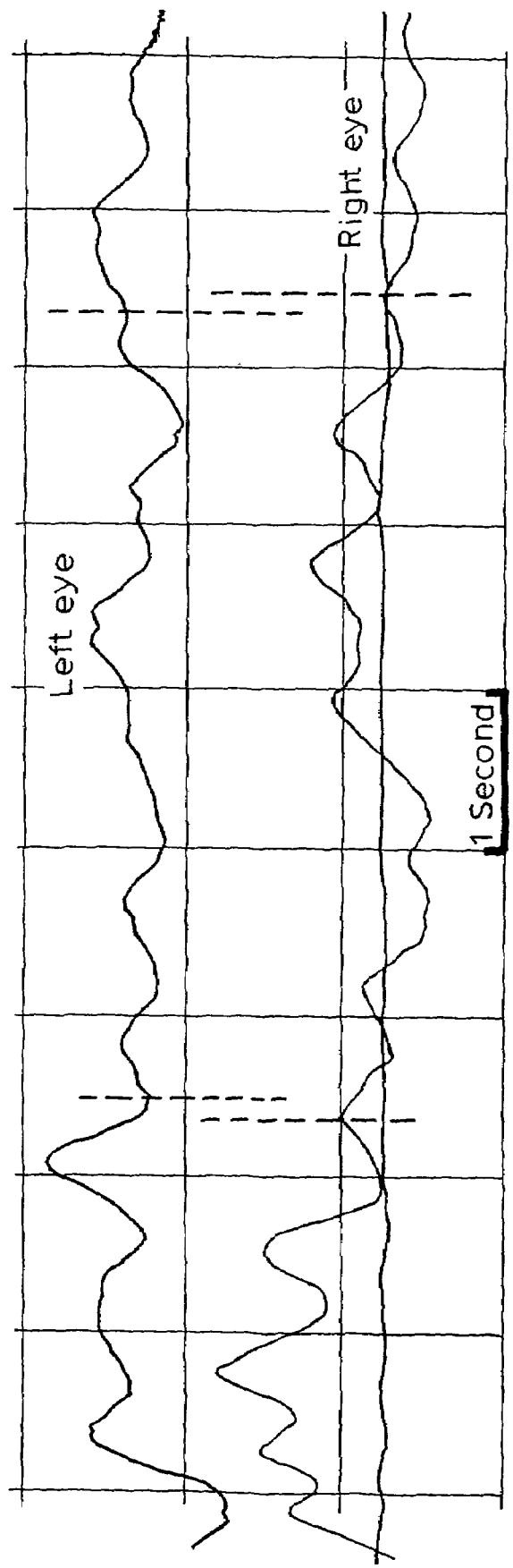
FIG. 4 is an example of a graphical output of this invention relating to eye movement for the left and right eyes.

FIG. 4 illustrates slow eye movements of a sleep deprived subject with eyes open. There is a phase difference between the left and right eyes equivalent to 150 milliseconds whereas movements of the two eyes are usually coordinated to within about 10 milliseconds.

Figure 8:
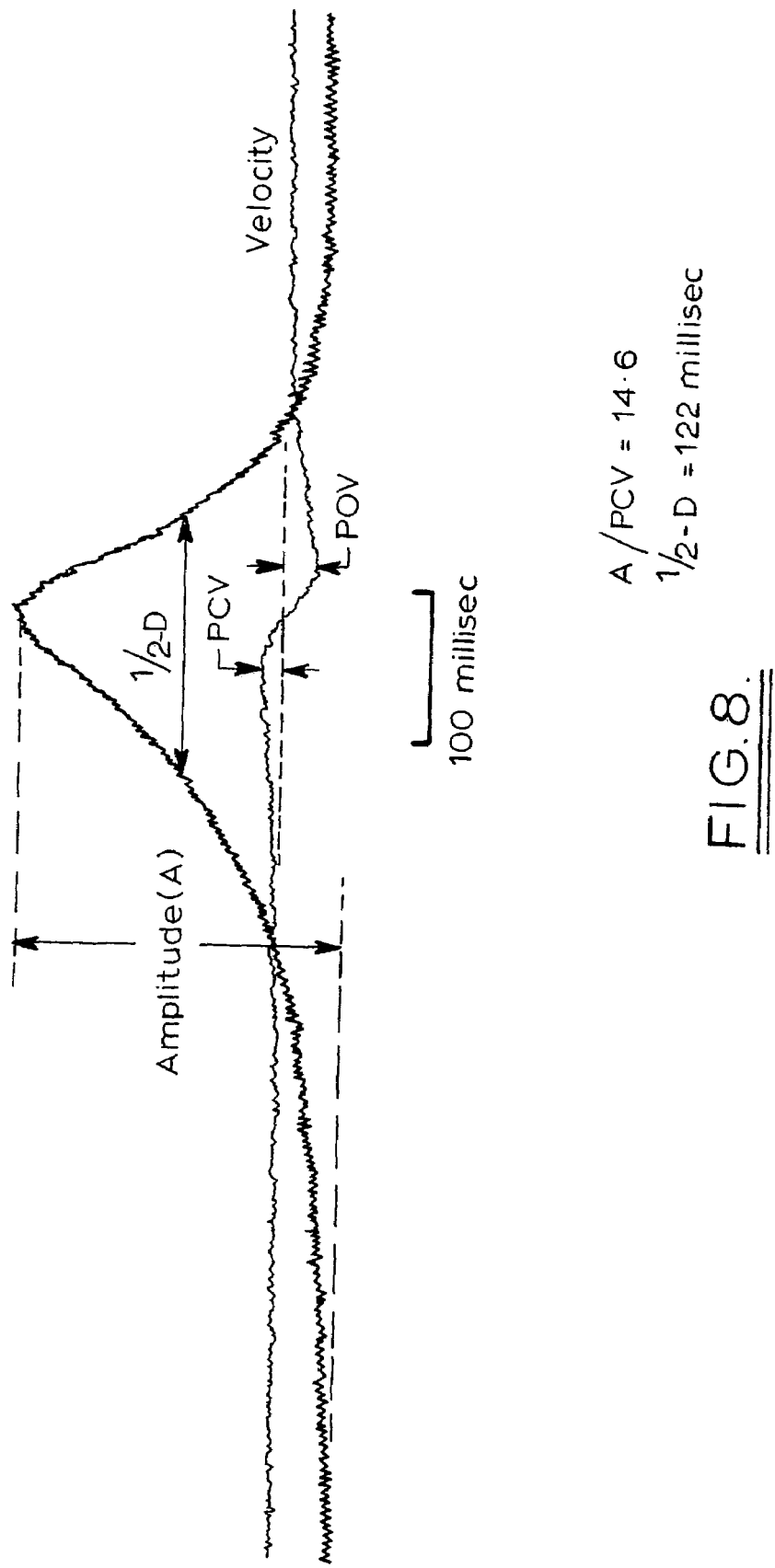
FIG. 8 illustrates the signal from a slow, partial blink of a sleep deprived subject.

Also detected are the slow drifting and poorly coordinated eye movements that are a hall mark of drowsiness as shown in FIG. 8. These movements begin early in the drowsiness state usually several minutes before electro encephalogram (EEG) measurements indicate sleep onset.

The reflected light may be analysed for saccade duration over a range of frequencies or a range of time domains. Saccade duration for normal alert eye movement is 5–70 milliseconds while slow eye movement indicative of drowsiness is of the order of 1–5 seconds. In alert subjects saccades are synchronised to within 10 milliseconds and blinks within 20 milliseconds but in drowsiness the coordination is reduced and the slow eye movements of drowsiness are often asynchronous by 50 to 200 or more milliseconds.

The preferred method is to analyse the reflectance signals to derive the blink amplitude and velocity values from the signals of detector 14.

Figure 5:
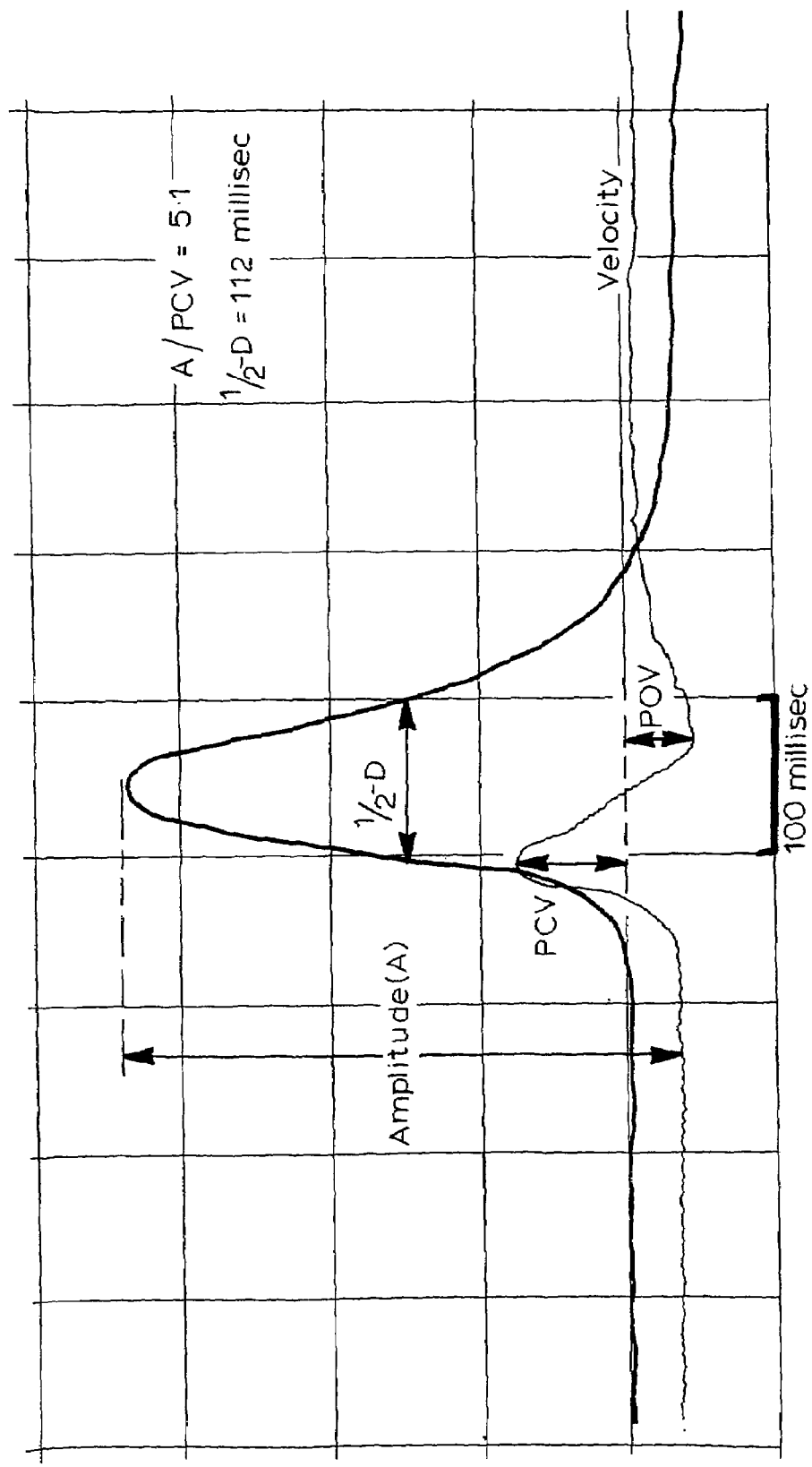
FIG. 5 illustrates a graph used to determine the blink amplitude velocity ratio (BAVR)

FIG. 5 illustrates the peak closing velocity (PCV) and the peak opening velocity (POV) of a normal blink. The peak closing velocity is greater than the peak opening velocity. Duration of blinks is preferably measured at half the amplitude (½ D) of the blink because of difficulty in determining when a blink ends. A normal ½ D is about 110+/−milliseconds.

The device of this invention and the analysis system is able to differentiate between grimaces that involve forced closure or opening of the eyes. Drowsy subjects do this to alleviate discomfort of their eyes. Grimaces may be separated from blinks in calculating BAVR's and they can be separated from spontaneous blinks regardless of duration. This means that faking of drowsiness may also be detected.

The analysis is carried out on a computer in cable or wireless communication with the LEDs and detectors. The software filters out the signals to provide patterns of eye movements at differing frequencies.

The method of analysis of the data uses ratio of the amplitude of each eye/eyelid movement to its peak velocity. For saccades there is only one such velocity while for blinks there are two namely closure velocity and opening velocity. It is preferred to use only the peak velocity of the eyelid closure as it varies in an understandable way, and opening velocity less so. The ratios are called the saccadic amplitude to velocity ratio (SAVR) illustrated graphically in FIG. 7 and the blink amplitude to velocity ratio (BAVR) illustrated graphically in FIG. 6, respectively.

Figure 6:
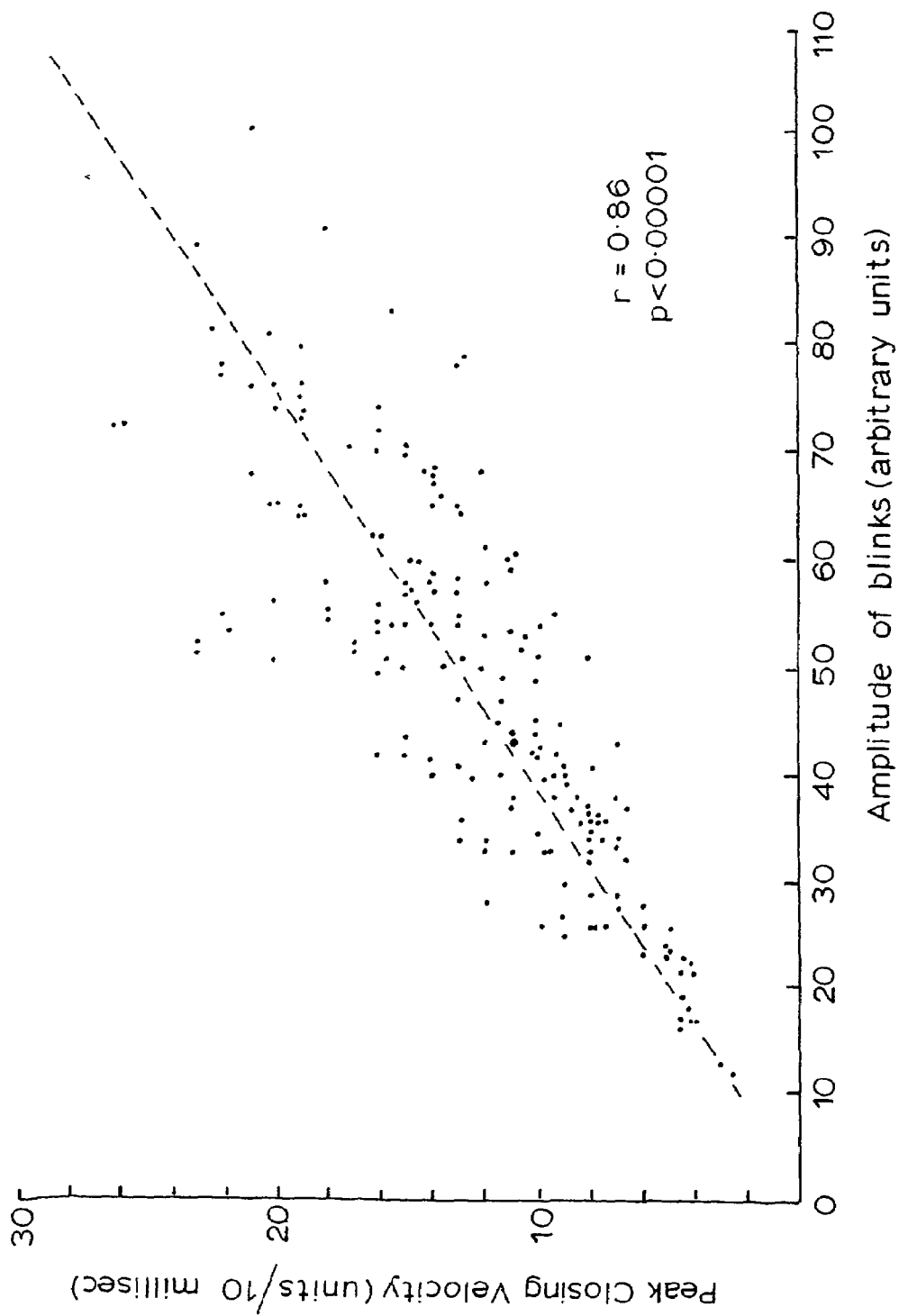
FIG. 6 illustrates a graph used to determine the saccade amplitude velocity ratio (SAVR)
Figure 7:
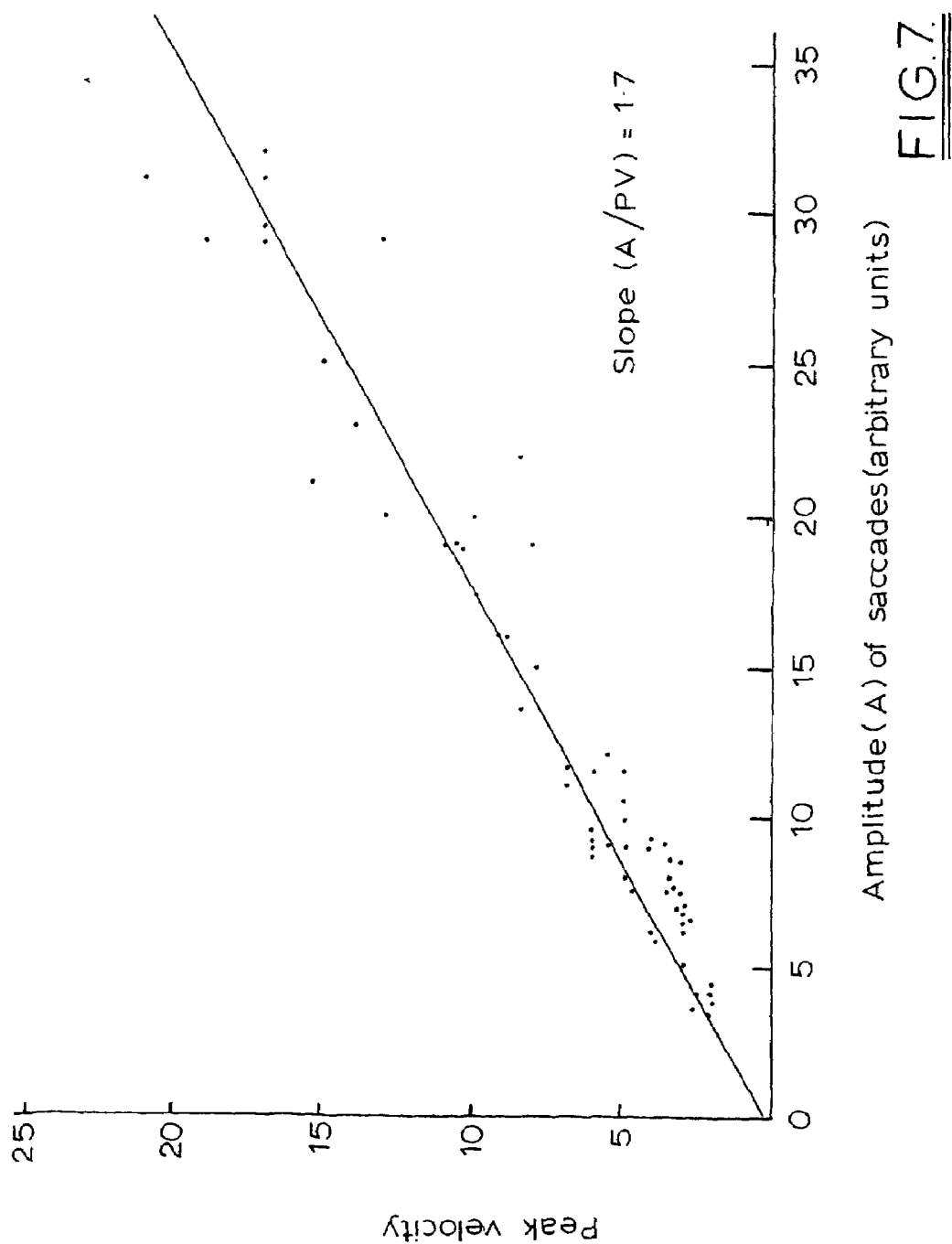
FIG. 7 illustrates the difference between the opening and closing velocity of blinks.

FIG. 6 shows the relationship between the blink amplitude and peak closing velocity for 200 blinks in 12 alert over a 30 second period. FIG. 7 shows that in alert subjects the peak velocity of saccades is linearly related to the amplitude but this is a different relationship from that with blinks.

Figure 9:
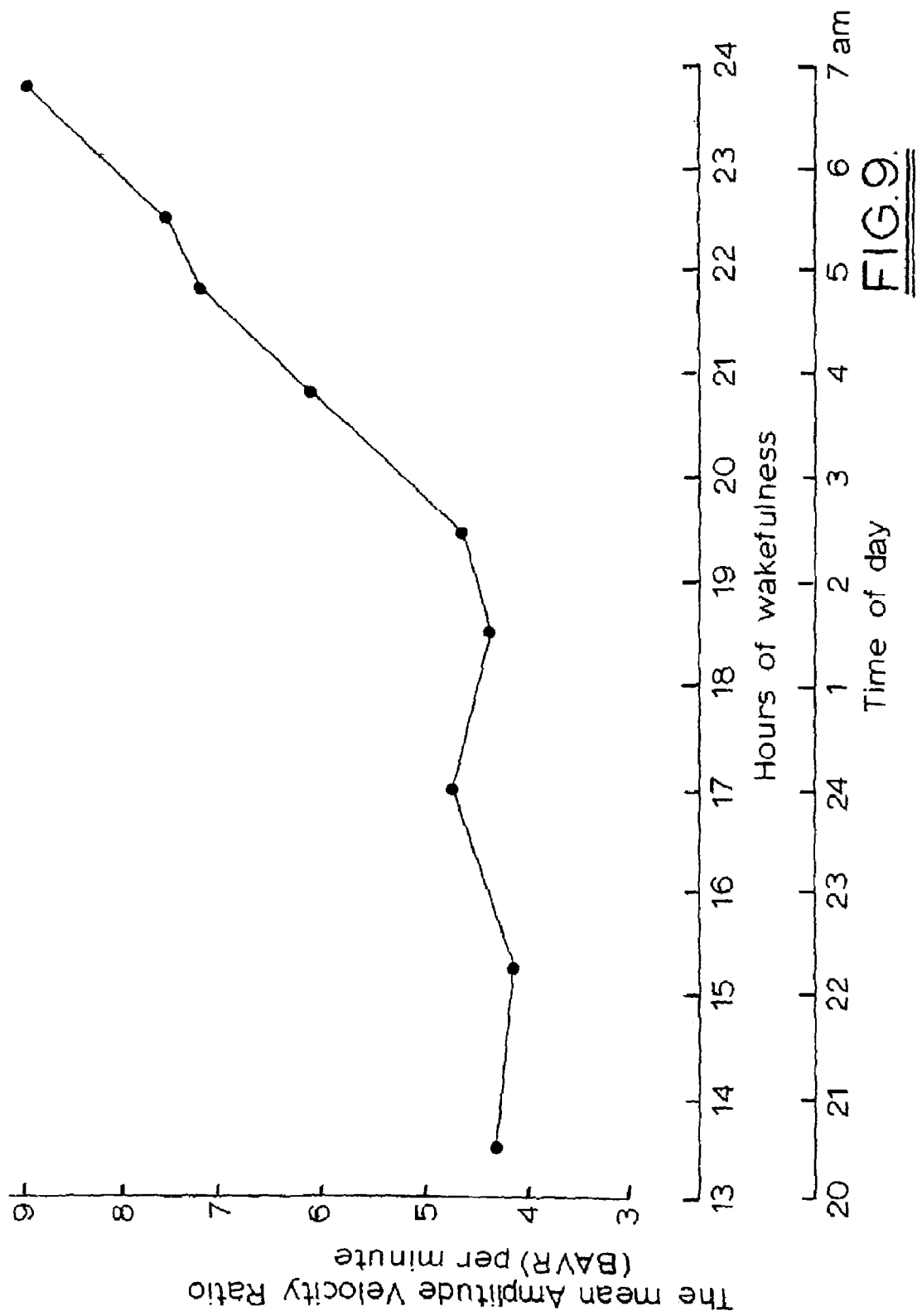
FIG. 9 illustrates the BAVR per minute plotted during a 10 minute performance test done repeatedly during sleep deprivation over night.

These ratios are independent of the set up conditions and the exact location of the transducers during the measurement (about 100 milliseconds).The SAVR reflects the contractile properties of the extra-ocular muscles and the BAVR reflects the contractile properties of the orbicularis muscles. These properties are influenced directly by the state of activation/deactivation of the central nervous system. The ratios increase progressively (up to 40 or more for the BAVR) as the level of drowsiness increases. Tests indicate that normal BAVR's are in the range of about 4.0+/−. BAVR increases before subjects begin to fail to respond because of drowsiness during in performance tests (see FIG. 9). FIG. 9 shows that for this subject there was no significant change in BAVR until after 20 hours of wakefulness after which it begins to increase progressively.

In drowsy subjects BAVR can vary widely in a matter of seconds. A mean BAVR or similar measure can be calculated in relation to any time scale from seconds to hours. The mean BAVR and the number of times individual BAVRs exceed the normal range as well as the total duration of such episodes per unit of time is measured and used to assess alertness. These measurements are then related to those previously recorded in subjects with blood alcohol levels preferably at 0.01% intervals to give an alertness measure based on blood alcohol equivalent levels.

Figure 10:
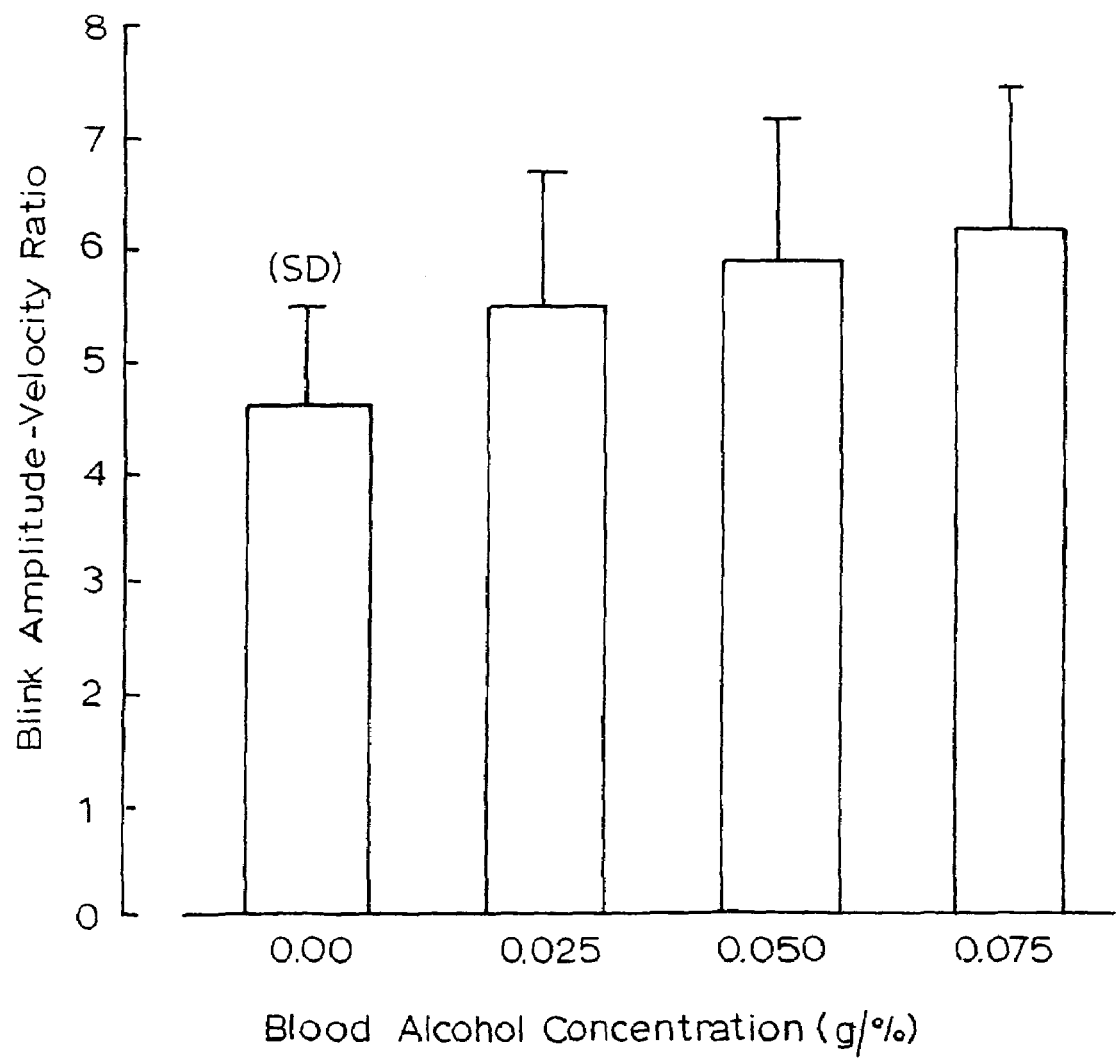
FIG. 10 illustrates the relationship between mean BAVR and blood alcohol concentration.

FIG. 10 illustrates the indicative relationship between the measured BAVR and blood alcohol concentration. A blood alcohol conc'n of 0.05% is approximately equivalent to a BAVR of 6.

Drowsiness is quantified over a period of seconds or minutes by a combination of he following variables:
- measurement and comparison of BAVR
- whether saccades are normal or abnormal based on SAVR and their frequency per unit of time
- the presence and duration of slow eye movements with impaired binocular coordination
- whether the eyelids are open or closed and for what proportion of time
- the presence of drooping or wavering eyelids as indicated by high BAVR
- the degree of binocular coordination including vestibular-ocular and smooth pursuit eye movements which are required for clear vision when driving a vehicle
- the frequency of long duration blinks and other eyelid closures with high BAVRs and their cumulative duration per unit of time
- the frequency of voluntary grimaces involving forced closure or opening of the eyes the duration of unusually long periods of ocular quiescence (many seconds) without eye or eyelid movements particular levels of drowsiness can be equated with particular blood alcohol concentrations From the above it can be seen that this invention provides a unique means of providing an alertness measure based on legal definitions of fitness to operate machinery or drive vehicles.

The method and apparatus described may be varied or modified to suit the particular application or equipment being used without departing from the fundamental elements of the method and device defined.

The invention claimed is:

1. An alertness monitoring system which includes:
   a) means to measure velocity and amplitude of eyelid and eye movement;
   b) storage means to continuously record the measurements;
   c) a data processor to calculate the blink amplitude to velocity ratio and/or the saccade amplitude to velocity ratio and compare the measurements against a predetermined scale, said scale being averaged measurements of the eye and eyelid movement parameters for a sample population measured against predetermined incremental blood alcohol levels;
   d) a display for showing the alertness measurement based on the scale; or
   e) an alarm means triggered by the scale reading reaching a predetermined limit based on the blood alcohol level scale.

2. An alertness system as claimed in claim 1 in which at least one infrared pulse emitter and one infrared detector is mounted on at least one eye.

3. An alertness system as claim 2 in which the detector measures the total level of light immediately before each pulse is transmitted and subtracts this from a combined level of the measured reflectance during the pulse.

4. A method of measuring alertness in which the eye movements of a subject are analyzed using reflected infrared light pulses to obtain measurements of the blink amplitude to velocity ratio and/or the saccade amplitude to velocity ratio averaged over predetermined periods of time and measuring the deviation of the average from a predetermined average for alert subjects.

5. A method as claimed in claim 4 in which the measured blink amplitude to velocity ratio and the saccade amplitude to velocity ratio values are related to a scale of blood alcohol content equivalent values.

6. A method as claimed in claim 5 in which the reflected light pulses are detected at two locations on each eye.

7. A method as claimed in claim 5 in which one location detects reflectance associated with eyelid movement and the second location detects reflectance associated with saccadic movement.

8. An alertness measuring system for a subject which includes:
   a) an infrared pulse emitter adapted to be located adjacent at least one eye of a subject;
   b) at least one reflected light detector located adjacent said emitter;
   c) means to transmit the detector signals;
   d) data processing means to receive die detector signals and to subtract a total level of light immediately before each pulse is transmitted from the combined level of the measured reflectance after the pulse to provide a reflectance measurement;
   e) said data processing means analyzing said reflectance measurement to calculate the blink amplitude to velocity ratio and/or the saccade amplitude to velocity ratio and compare the measurements against a predetermined scale.

9. An alertness measuring system as claimed in claim 8 in which the reflected light pulses are detected at two locations on each eye.

10. An alertness measuring system as claimed in claim 9 which one location detects reflectance associated with eyelid movement and the second location detects reflectance associated with saccadic movement.

11. An alertness measuring system as claimed in claim 10 in which the data processing system analyzes the reflectance signals to obtain measures of the blink amplitude to velocity ratio and/or the saccade amplitude to velocity ratio) averaging these over predetermined periods of time and measuring the deviation of the average from a predetermined average for alert subjects.

12. An alertness measuring system as claimed in claim 11 in which the measured blink amplitude to velocity ratio and the saccade amplitude to velocity ratio values are converted to a scale of blood alcohol content equivalent values.

13. An alertness measuring system as claimed in claim 12 which includes a display for displaying the alertness measurement or an alarm triggered by the scale reading reaching a predetermined limit based on the blood alcohol level scale.

14. An alertness monitoring system which includes:
   a) means to measure eyelid and eye movement;
   b) storage means to continuously record the measurements;
   c) a data processor in which the recorded measurements are analyzed to obtain measures of the blink amplitude to velocity ratio and/or the saccade amplitude to velocity ratio and measuring the deviation from a predetermined average for alert subjects;
   d) a display for showing the analyzed measurements; or
   e) an alarm means triggered when a predetermined measurement threshold is crossed.

15. An alertness monitoring system as claimed in claim 14 in which the measured blink amplitude to velocity ratio and the saccade amplitude to velocity ratio values are related to a scale of blood alcohol content equivalent values.

16. A method of measuring alertness, the method comprising:
   measuring velocity and amplitude of eyelid and eye movement of a subject;
   calculating an eyelid movement amplitude to velocity ratio and/or an eye movement amplitude to velocity ratio;
   calculating an average of one or both ratios over at least one predetermined period of time; and
   determining a deviation of the calculated averages from predetermined averages for alert subjects; and
   triggering an alarm if the deviation of the determined average from a predetermined average reaches or exceeds a predetermined limit.

17. A method as claimed in claim 16 in which at least two infrared detectors are used and the reflected light pulses are detected at at least two locations on at least one eye.

18. A method as claimed in claim 17 in which at least one location detects reflectance associated with eyelid movement and at least one other location detects reflectance associated with eye movement.

* * * * *